United States Patent
Lin et al.

(10) Patent No.: US 11,904,257 B2
(45) Date of Patent: Feb. 20, 2024

(54) SYSTEM FOR INCREASING EXTRACTION OF ACTIVE INGREDIENT

(71) Applicant: TCI CO., LTD., Taipei (TW)

(72) Inventors: Yung-Hsiang Lin, Taipei (TW); Chien-Yu Lu, Taipei (TW); Jin-Jia Wang, Taipei (TW)

(73) Assignee: TCI CO., LTD., Taipei (TW)

( * ) Notice: Subject to any disclaimer, the term of this patent is extended or adjusted under 35 U.S.C. 154(b) by 548 days.

(21) Appl. No.: 17/169,556

(22) Filed: Feb. 8, 2021

(65) Prior Publication Data

US 2022/0001296 A1    Jan. 6, 2022

(30) Foreign Application Priority Data

Jul. 6, 2020    (CN) .......................... 202021303350.2

(51) Int. Cl.
*B01D 11/02*    (2006.01)
*A61K 36/21*    (2006.01)
(Continued)

(52) U.S. Cl.
CPC ............ *B01D 11/02* (2013.01); *A61K 31/352* (2013.01); *A61K 31/706* (2013.01); *A61K 36/21* (2013.01);
(Continued)

(58) Field of Classification Search
CPC . B01D 11/02; B01D 11/0257; B01D 11/0288; A61K 31/352; A61K 31/706;
(Continued)

(56) References Cited

U.S. PATENT DOCUMENTS

2016/0081976 A1 *    3/2016    Bromley ................ A61K 31/12
514/168

FOREIGN PATENT DOCUMENTS

CN    105111256 A    * 12/2015
CN    107375055 A    * 11/2017
(Continued)

OTHER PUBLICATIONS

Machine-generated English translation of CN 105111256, generated on Sep. 19, 2023.*
(Continued)

*Primary Examiner* — Fred Prince
(74) *Attorney, Agent, or Firm* — Chich-Mei Wang

(57) ABSTRACT

A system for increasing the extraction of an active ingredient includes a vacuum quick-dissolving tank, a mixer, a solid-liquid separator, and a homogenizer. The vacuum quick-dissolving tank receives a sample. The mixer is connected to the vacuum quick-dissolving tank, and provides an aqueous solvent to be mixed with the sample. Heating, cooling, stirring, and vacuuming in the vacuum quick-dissolving tank make the sample dissolve and emulsify repeatedly between the vacuum quick-dissolving tank and the mixer to produce a mixture, which is output by the vacuum quick-dissolving tank. The solid-liquid separator receives the mixture output from the vacuum quick-dissolving tank for solid-liquid separation, and outputs an isolated sample liquid. The homogenizer receives the sample liquid output from the solid-liquid separator, performs high-pressure homogenization to obtain an extract liquid containing an active ingredient, and outputs the extract liquid. The homogenizer can increase the content of the active ingredient in the extract liquid.

14 Claims, 3 Drawing Sheets

(51) Int. Cl.
*A61K 31/70* (2006.01)
*A61K 36/81* (2006.01)
*B01F 23/41* (2022.01)
*B01F 25/45* (2022.01)
*A61K 36/88* (2006.01)
*A61K 31/706* (2006.01)
*A61K 31/352* (2006.01)

(52) U.S. Cl.
CPC .............. *A61K 36/81* (2013.01); *A61K 36/88* (2013.01); *B01D 11/0257* (2013.01); *B01D 11/0288* (2013.01); *B01F 23/41* (2022.01); *B01F 25/45* (2022.01); *A61K 2236/331* (2013.01); *A61K 2236/37* (2013.01); *B01F 23/4146* (2022.01)

(58) Field of Classification Search
CPC ........ A61K 36/21; A61K 36/81; A61K 36/88; A61K 2236/331; A61K 2236/37; B01F 23/41; B01F 25/45; B01F 23/4146
USPC .................................. 210/177, 178, 180, 181
See application file for complete search history.

(56) References Cited

FOREIGN PATENT DOCUMENTS

| CN | 111035697 A | * | 4/2020 |
| CN | 111838653 A | * | 10/2020 |
| WO | WO 2004-019961 A | * | 3/2004 |
| WO | WO 2019/057927 A1 | * | 3/2019 |

OTHER PUBLICATIONS

Machine-generated English translation of CN 111035697, generated on Sep. 19, 2023.*
Machine-generated English translation of CN 111838653, generated on Sep. 19, 2023.*
Machine-generated English translation of CN 107375055, generated on Dec. 10, 2023.*
Machine-generated English translation of CN 111838653, generated on Dec. 10, 2023.*

\* cited by examiner

SYSTEM FOR INCREASING EXTRACTION OF ACTIVE INGREDIENT

CROSS-REFERENCE TO RELATED APPLICATION

This non-provisional application claims priority under 35 U.S.C. § 119(a) to Patent Application No. 202021303350.2 filed in China, P.R.C. on Jul. 6, 2020, the entire contents of which are hereby incorporated by reference.

BACKGROUND

Technical Field

The present invention relates to a system that can extract an active ingredient from a sample, and specifically, to a system that can extract an active ingredient from a sample and includes a homogenizer for high-pressure homogenization.

Related Art

Plants are known to contain various active ingredients beneficial to the human body, for example, an anthocyanidin in black tomato, serotonin in banana peel, and a betalain, betaxanthin, polyphenol, and flavone in *Chenopodium formosanum*. It is known that active ingredients can be extracted from plants by system equipment utilizing an impregnation method, a pressing method, a solvent extraction method, an ultrasound extraction method or a supercritical extraction method. However, existing system equipment still has problems to be resolved, for example, excessive time consumption, low extraction efficiency, and difficulty in mass production.

In view of the disadvantages in existing extraction technologies, the present invention provides a system that can extract an active ingredient from a sample and includes a homogenizer for high-pressure homogenization, to effectively extract a substantial amount of an active ingredient from a sample.

SUMMARY

The present invention provides a system for increasing the extraction of an active ingredient, including a vacuum quick-dissolving tank, a mixer, a solid-liquid separator, and a homogenizer. The vacuum quick-dissolving tank receives a sample. The mixer is bidirectionally connected to the vacuum quick-dissolving tank, and provides an aqueous solvent to be mixed with the sample. Heating, cooling, stirring, and vacuuming in the vacuum quick-dissolving tank make the sample dissolve and emulsify repeatedly between the vacuum quick-dissolving tank and the mixer to produce a mixture, which is output by the vacuum quick-dissolving tank. The solid-liquid separator receives the mixture output from the vacuum quick-dissolving tank for solid-liquid separation, and outputs an isolated sample liquid in a liquid phase. The homogenizer receives the sample liquid output from the solid-liquid separator, performs high-pressure homogenization to obtain an extract liquid containing an active ingredient, and outputs the extract liquid. The homogenizer can increase the content of the active ingredient in the extract liquid.

In some embodiments, the homogenizer receives the sample liquid output from the solid-liquid separator, and performs homogenization to obtain a crude extract liquid containing the active ingredient.

More specifically, in some embodiments, the system further includes a sieving tool, receiving the crude extract liquid obtained by the homogenizer, and performing sieving to obtain a filtrate, which is output back to the homogenizer for high-pressure homogenization, where a screen of 20 mesh to 400 mesh is used in the sieving.

More specifically, in some embodiments, the active ingredient is an anthocyanidin, the sample is one of black tomato, sea grape, and red onion, and the homogenization is performed at a temperature of 35° C. to 45° C.

More specifically, in some embodiments, the active ingredient is serotonin, the sample is one of banana, longan peel, and ginseng, and the homogenization is performed at a temperature of 80° C. to 90° C.

More specifically, in some embodiments, the active ingredient includes at least a betalain, the sample is one of *Chenopodium formosanum* and early-pick guava fruit, and the homogenization is performed at a temperature of 80° C. to 90° C.

In some embodiments, the high-pressure homogenization of the homogenizer is performed under a pressure of 400 bar to 2,000 bar.

In some embodiments, the high-pressure homogenization of the homogenizer is performed at a temperature of 25° C. to 40° C.

In some embodiments, the high-pressure homogenization of the homogenizer is performed at a temperature of 80° C. to 90° C.

In some embodiments, the system further includes a pulverizer, where the pulverizer receives a raw material, performs pulverization on the raw material to obtain the sample, and outputs the sample to the vacuum quick-dissolving tank.

In some embodiments, the system further includes a peeler, where the peeler receives a raw material, and performs peeling on the raw material to obtain and output a peeled object.

More specifically, in some embodiments, the system further includes a rough crusher, where the rough crusher receives the peeled object from the peeler, performs crushing to obtain the sample, and outputs the sample to the vacuum quick-dissolving tank.

In some embodiments, the aqueous solvent is water.

The present invention provides a system that can extract an active ingredient from a sample and includes a homogenizer for high-pressure homogenization, to effectively extract substantial amounts of an active ingredient from a sample.

DETAILED DESCRIPTION

Figure 1:
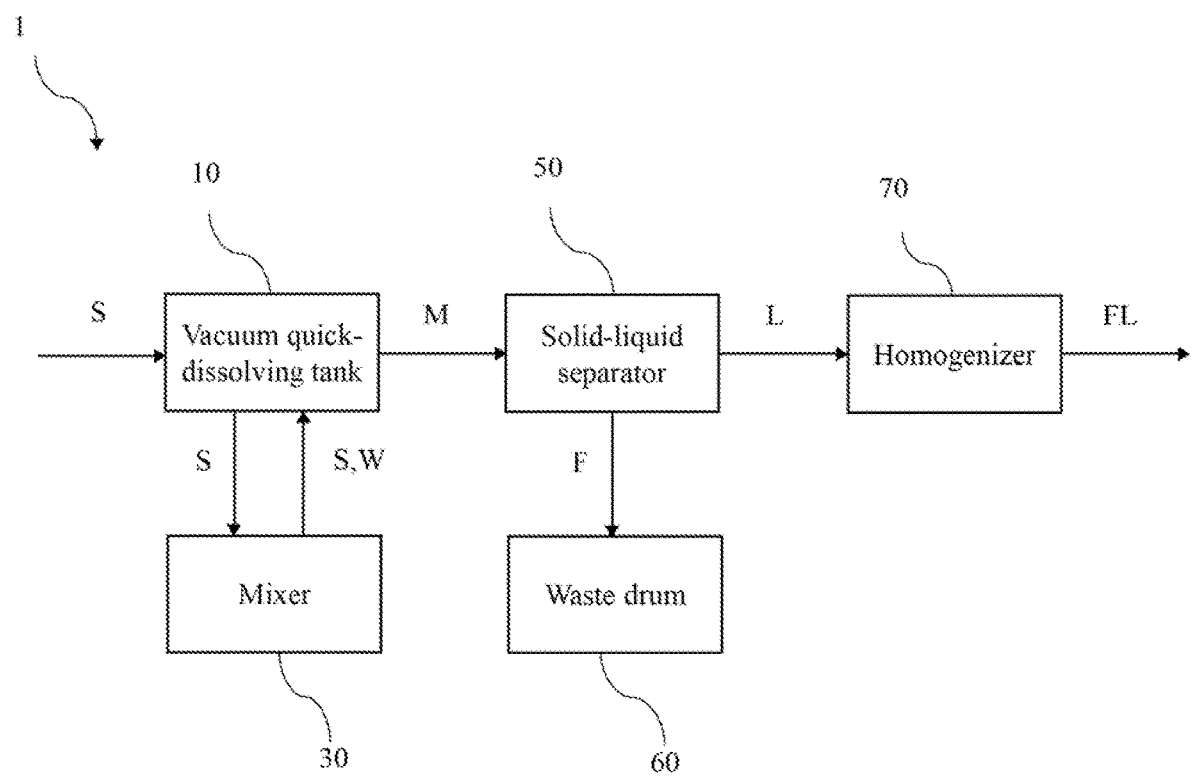
FIG. 1 is a diagram of a system for extracting an active ingredient.

FIG. 1 is a diagram of a system for extracting an active ingredient. As shown in FIG. 1, a system 1 for increasing the extraction of an active ingredient includes a vacuum quick-dissolving tank 10, a mixer 30, a solid-liquid separator 50, and a homogenizer 70. The vacuum quick-dissolving tank 10 receives a sample S. The mixer 30 is bidirectionally connected to the vacuum quick-dissolving tank 10, and provides an aqueous solvent W to be mixed with the sample S. Heating, cooling, stirring, and vacuuming in the vacuum quick-dissolving tank 10 make the sample S dissolve and emulsify repeatedly between the vacuum quick-dissolving tank 10 and the mixer 30 to produce a mixture, which is output by the vacuum quick-dissolving tank 10. Herein, the aqueous solvent W used in the mixer 30 is water. However, this is only an example for description, and the present invention is not limited thereto in practice.

The solid-liquid separator 50 receives the mixture M output from the vacuum quick-dissolving tank 10 for solid-liquid separation, and outputs an isolated sample liquid L in a liquid phase. In addition, the system 1 for increasing the extraction of an active ingredient may include a waste drum 60. The waste drum 60 receives solid waste residues F from the solid-liquid separator 50. The homogenizer 70 receives the sample liquid L from the solid-liquid separator 50, and performs high-pressure homogenization to obtain an extract liquid FL containing the active ingredient. By means of a high-pressure process, the homogenizer 70 can increase the content of the active ingredient in the extract liquid FL. Herein, the high-pressure homogenization of the homogenizer 70 is performed under a pressure of 400 bar to 2,000 bar and preferably under a pressure of 400 bar to 450 bar. In addition, the temperature of the high-pressure homogenization is adjusted according to different samples. For example, for *Chenopodium formosanum* and banana, the homogenization is performed at a temperature of 80° C. to 90° C., and for black tomato, the homogenization is performed at a temperature of 25° C. to 40° C.

Figure 2:
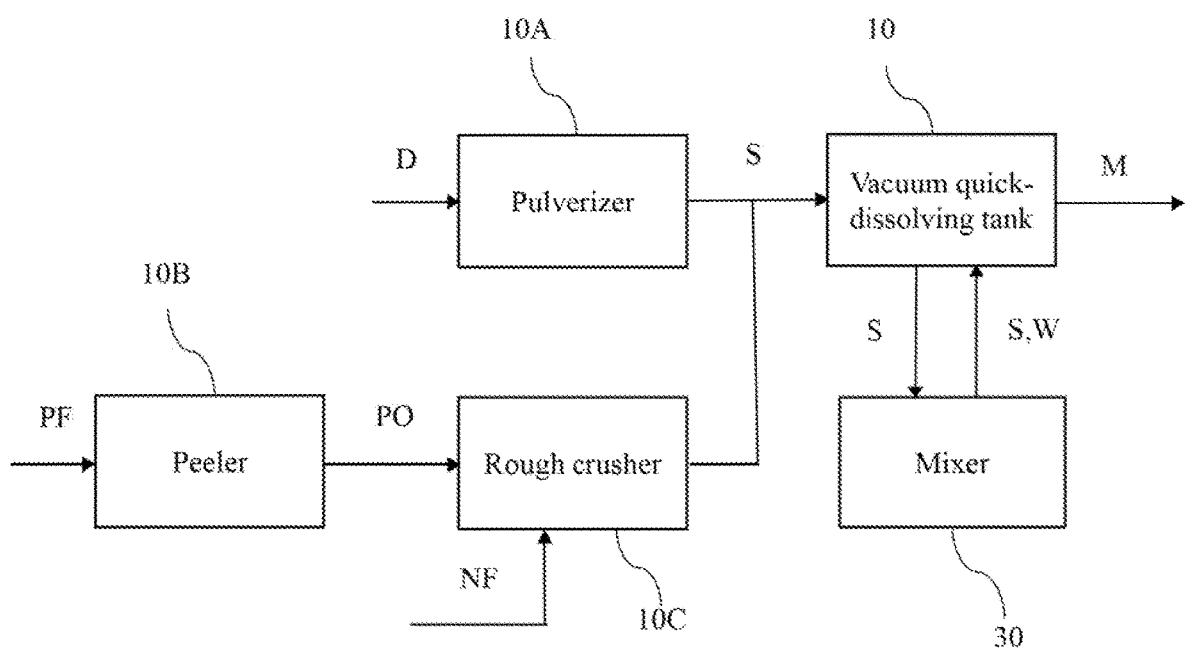
FIG. 2 is a diagram of a system for treating a raw material.

FIG. 2 is a diagram of a system for treating a raw material. In some embodiments, to improve the efficiency of mixing the sample S and the aqueous solvent W, the system 1 for increasing the extraction of an active ingredient may include a pulverizer 10A, a peeler 10B, and a rough crusher 10C that separately perform treatment on a raw material O to obtain a sample S. The raw material O includes a dry material D, a fresh material that requires peeling PF, and fruit that does not require peeling NF. The dry material D is one of *Chenopodium formosanum*, mandarin orange peel, lotus leaf, mountain hawthorn, and Chinese yam. As shown in FIG. 2, the pulverizer 10A receives the dry material D, performs pulverization on the dry material D to obtain the sample S, and outputs the sample S to the vacuum quick-dissolving tank 10.

Referring to FIG. 2, the fresh material that requires peeling PF is a banana. The peeler 10B receives the fresh material that requires peeling PF, performs peeling on the fresh material that requires peeling PF to obtain a peeled object PO, and outputs the peeled object. The rough crusher 10C receives the peeled object PO from the peeler 10B, performs crushing to obtain the sample S, and outputs the sample S to the vacuum quick-dissolving tank 10.

Referring to FIG. 2 again, the fruit that does not require peeling NF is one of black tomato, early-pick tangerine fruit, early-pick mango fruit, and early-pick guava fruit. In some embodiments, the rough crusher 10C receives the fruit that does not require peeling NF, performs crushing on the fruit that does not require peeling NF to obtain the sample S, and outputs the sample S to the vacuum quick-dissolving tank 10.

In general, mango is used as an example. The growth of mango fruit includes the following four stages: (1) Young fruit stage: After a mango flower withers, a fruit begins to grow slowly and is green. (2) Rapid growth stage: The fruit rapidly grows fleshy, and the starch in the pulp gradually accumulates. (3) Ripening stage: After the inner peel of the fruit hardens, the fruit enters the ripening stage. At this time, the shape of the fruit hardly changes, but the weight of the fruit continues to increase. Some physical and chemical changes still take place. For example, the hardness of the fruit decreases, the sugar content increases, and the peel turns yellow, so that the fruit approaches a fully ripe and edible stage. (4) Aging stage: After the fruit is fully ripe, the fruit begins to age. The early-pick fruit mentioned in this application is a fruit that has not entered the ripening stage, that is, a fruit in the young fruit stage or in the rapid growth stage.

Figure 3:
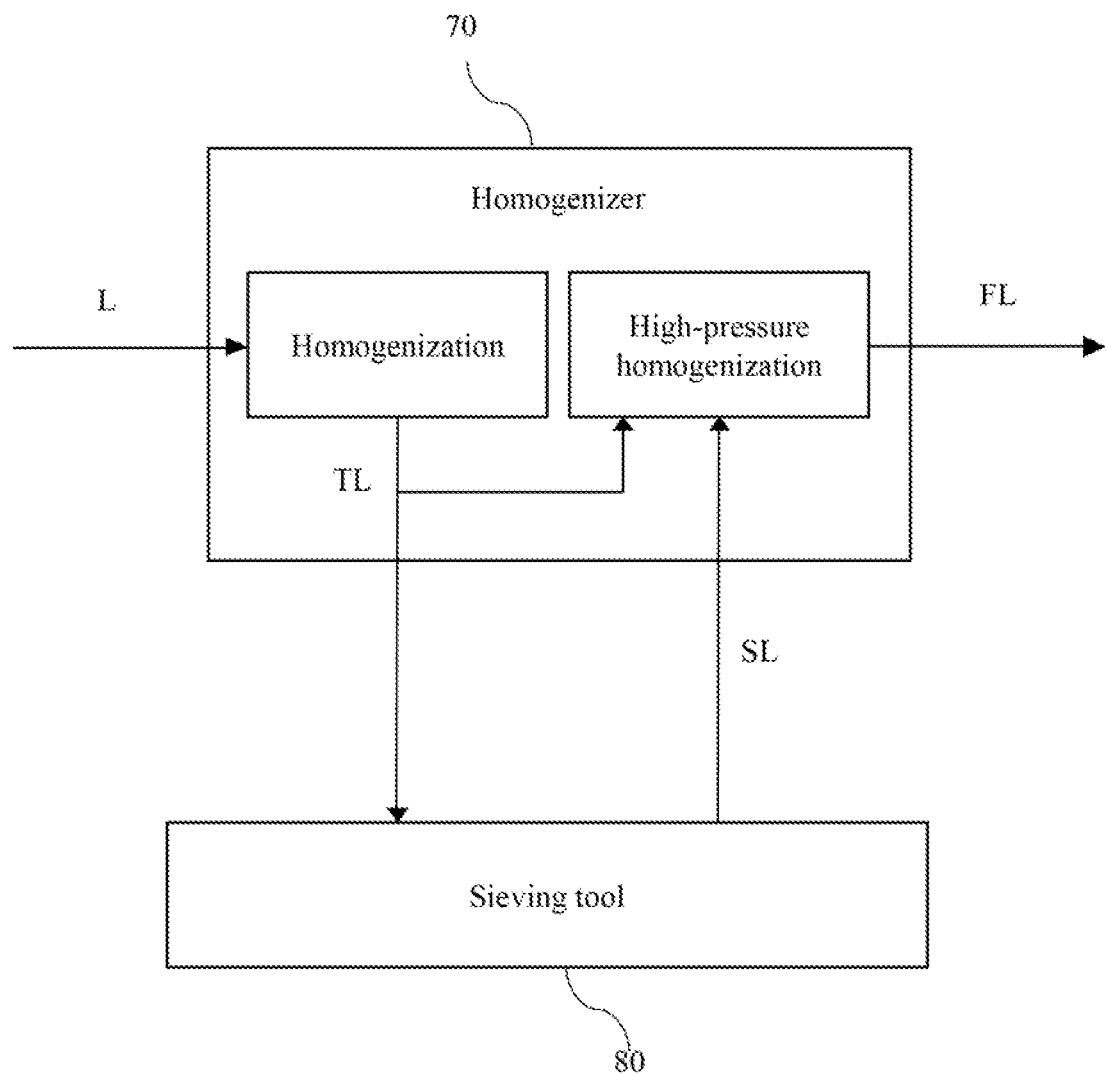
FIG. 3 is a diagram of a homogenization system.

FIG. 3 is a diagram of a homogenization system. In some embodiments, as shown in FIG. 3, the homogenizer 70 receives the sample liquid L output from the solid-liquid separator 50, and performs homogenization under atmospheric pressure to obtain a crude extract liquid TL containing an active ingredient. The homogenization may be performed once or repeatedly as required. For example, to improve the homogenization effect, primary homogenization using a thick homogenization bit is first performed on the sample liquid L, secondary homogenization using a thin homogenization bit is then performed, and high-pressure homogenization is finally performed on the crude extract liquid TL containing the active ingredient to obtain the extract liquid FL containing the active ingredient.

Referring to FIG. 3 again, more specifically, the system 1 for increasing the extraction of an active ingredient may further include a sieving tool 80. Sieving may be performed as required prior to the high-pressure homogenization. The sieving tool 80 receives the crude extract liquid TL obtained by the homogenizer 70, and removes large remaining particles in the crude extract liquid TL, so as to improve the efficiency of the high-pressure homogenization. The sieving tool 80 obtains a filtrate SL through sieving, and outputs the filtrate back to the homogenizer 70 for high-pressure homogenization to obtain and output the extract liquid FL containing the active ingredient. The mesh size of the screen used in the sieving depends on the sizes of the remaining particles. In general, the sieving tool 80 includes a screen of 20 mesh to 400 mesh. However, this is only an example for description, and the present invention is not limited thereto in practice.

Referring to FIG. 1, FIG. 2, and FIG. 3 again, in the first embodiment, the active ingredient includes at least one of betacyanin, betaxanthin, polyphenol, flavone, polysaccharide, saponin, tannin, and synephrine. A sample S is one of *Chenopodium formosanum*, coffee cherry, early-pick *Ziziphus mauritiana* fruit, alpinia galanga, wasabi leaves, *Passiflora caerulea* seed, colored glaze fruit, Chinese mosla herb, Citrus aurantium, *Ascophyllum Nodosum*, pineapple, golden berry, enoki, Chinese yam, early-pick mango fruit, and early-pick tangerine fruit. In this example, the active ingredient is betacyanin, and the sample S is *Chenopodium formosanum*. A pulverizer 10A performs pulverization on a raw material *Chenopodium formosanum* to obtain a *Chenopodium formosanum* sample, which is output to the vacuum quick-dissolving tank 10. The *Chenopodium formosanum* sample is mixed with an aqueous solvent W provided by the mixer 30, and dissolves repeatedly between the vacuum quick-dissolving tank 10 and the mixer 30 to produce a *Chenopodium formosanum* mixture.

The *Chenopodium formosanum* mixture is output to the solid-liquid separator 50 for solid-liquid separation to obtain a *Chenopodium formosanum* sample liquid, which is output to the homogenizer 70 for one or more times of homogenization as required. The homogenization is performed at a temperature of 80° C. to 90° C. to obtain a *Chenopodium formosanum* crude extract liquid, and the *Chenopodium formosanum* crude extract liquid is output to the sieving tool 80 for sieving to obtain a *Chenopodium formosanum* filtrate, which is then output back to the homogenizer 70 for high-pressure homogenization to obtain a *Chenopodium formosanum* extract liquid containing at least betacyanin.

Referring to FIG. 1, FIG. 2, and FIG. 3 again, in the second embodiment, the active ingredient is serotonin, and the sample S is one of banana, longan peel, and ginseng. The banana is used as an example herein. The peeler 10B performs peeling on a raw material banana to obtain banana peel, and outputs the banana peel to the rough crusher 10C to obtain a banana peel sample, which is output to the vacuum quick-dissolving tank 10, is mixed with an aqueous solvent W provided by the mixer 30, and dissolves repeatedly between the vacuum quick-dissolving tank 10 and the mixer 30 to produce a banana peel mixture.

The banana peel mixture is output to the solid-liquid separator 50 for solid-liquid separation to obtain a banana peel sample liquid, which is output to the homogenizer 70 for one or more times of homogenization as required. The homogenization is performed at a temperature of 80° C. to 90° C. to obtain a banana peel crude extract liquid. The banana peel crude extract liquid is then output to the sieving tool 80 for sieving to obtain a banana peel filtrate, which is then output back to the homogenizer 70 for high-pressure homogenization to obtain a banana peel extract liquid containing serotonin.

Referring to FIG. 1, FIG. 2, and FIG. 3 again, in the third embodiment, the active ingredient is an anthocyanidin, and the sample S is one of black tomato, sea grape, and red onion. The black tomato is used as an example herein. The rough crusher 10C performs crushing on a raw material black tomato to obtain a black tomato sample, which is output to the vacuum quick-dissolving tank 10. The black tomato sample is mixed with the aqueous solvent W provided by the mixer 30, and dissolves repeatedly between the vacuum quick-dissolving tank 10 and the mixer 30 to produce a black tomato mixture.

The black tomato mixture is output to the solid-liquid separator 50 for solid-liquid separation to obtain a black tomato sample liquid, which is output to the homogenizer 70 for one or more times of homogenization as required. The homogenization is performed at a temperature of 35° C. to 45° C. to obtain a black tomato crude extract liquid, and the black tomato crude extract liquid is output to the sieving tool 80 for sieving to obtain a black tomato filtrate, which is then output back to the homogenizer 70 for high-pressure homogenization to obtain a black tomato extract liquid containing the anthocyanidin.

In view of the above examples, the system for increasing the extraction of an active ingredient including a homogenizer for high-pressure homogenization provided by the present invention can effectively improve the efficiency of extracting an active ingredient from a sample by using a system combination of the vacuum quick-dissolving tank 10, the mixer 30, the solid-liquid separator 50, and the homogenizer 70. As shown in Table 1, in the actual examples of *Chenopodium formosanum* and black tomato, it can be observed that the active ingredient that needs to be extracted is increased after homogenization.

TABLE 1

Results of extracting an active ingredient

| | Mean or not | Active ingredient |
|---|---|---|
| Chenopodium formosanum | No | Betalain 718.0-µg/g |
| | Yes | Betalain 738.0-µg/g |
| Black tomato | No | Anthocyanidin 1.30-µg/g |
| | Yes | Anthocyanidin 1.55-µg/g |

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A system for increasing an extraction of an active ingredient, comprising:
   a vacuum dissolving tank, receiving a sample;
   a mixer, bidirectionally connected to the vacuum dissolving tank, and providing an aqueous solvent to be mixed with the sample, wherein heating, cooling, stirring, and vacuuming in the vacuum dissolving tank make the sample dissolve and emulsify repeatedly between the vacuum dissolving tank and the mixer to produce a mixture, which is output by the vacuum dissolving tank;
   a solid-liquid separator, receiving the mixture output from the vacuum dissolving tank for solid-liquid separation, and outputting an isolated sample liquid in a liquid phase; and
   a homogenizer, receiving the sample liquid output from the solid-liquid separator, performing homogenization to obtain an extract liquid containing an active ingredient, and outputting the extract liquid, wherein the homogenizer is capable of increasing the content of the active ingredient in the extract liquid.

2. The system for increasing the extraction of an active ingredient according to claim 1, wherein the homogenizer receives the sample liquid output from the solid-liquid separator, and performs homogenization to obtain a crude extract liquid containing the active ingredient.

3. The system for increasing the extraction of an active ingredient according to claim 2, further comprising a sieving tool, receiving the crude extract liquid obtained by the homogenizer, and performing sieving to obtain a filtrate, which is output back to the homogenizer for homogenization, wherein a screen of 20 mesh to 400 mesh is used in the sieving.

4. The system for increasing the extraction of an active ingredient according to claim 2, wherein the active ingredient is an anthocyanidin, the sample is one of black tomato, sea grape, and red onion, and the homogenization is performed at a temperature of 35° C. to 45° C.

5. The system for increasing the extraction of an active ingredient according to claim 2, wherein the active ingredient is serotonin, the sample is one of banana, longan peel, and ginseng, and the homogenization is performed at a temperature of 80° C. to 90° C.

6. The system for increasing the extraction of an active ingredient according to claim 5, wherein the homogenization of the homogenizer is performed at a temperature of 80° C. to 90° C.

7. The system for increasing the extraction of an active ingredient according to claim 2, wherein the active ingredient comprises at least a betalain, the sample is one of *Chenopodium formosanum* and guava fruit, and the homogenization is performed at a temperature of 80° C. to 90° C.

8. The system for increasing the extraction of an active ingredient according to claim 1, wherein the homogenization of the homogenizer is performed under a pressure of 100 bar to 2,000 bar.

9. The system for increasing the extraction of an active ingredient according to claim 4, wherein the homogenization of the homogenizer is performed at a temperature of 25° C. to 40° C.

10. The system for increasing the extraction of an active ingredient according to claim 5 or 6, wherein the homogenization of the homogenizer is performed at a temperature of 80° C. to 90° C.

11. The system for increasing the extraction of an active ingredient according to claim 1, further comprising a pulverizer, wherein the pulverizer receives a raw material, performs pulverization on the raw material to obtain the sample, and outputs the sample to the vacuum dissolving tank.

12. The system for increasing the extraction of an active ingredient according to claim 1, further comprising a peeler, wherein the peeler receives a raw material, and performs peeling on the raw material to obtain and output a peeled object.

13. The system for increasing the extraction of an active ingredient according to claim 10, further comprising a rough crusher, wherein the rough crusher receives the peeled object from the peeler, performs crushing to obtain the sample, and outputs the sample to the vacuum dissolving tank.

14. The system for increasing the extraction of an active ingredient according to claim 1, wherein the aqueous solvent is water.

* * * * *